US007488595B2

(12) United States Patent
Hwang et al.

(10) Patent No.: US 7,488,595 B2
(45) Date of Patent: Feb. 10, 2009

(54) METHOD AND APPARATUS FOR AMPLIFICATION OF NUCLEIC ACID SEQUENCES USING IMMOBILIZED DNA POLYMERASE

(75) Inventors: Hyun Jin Hwang, Seoul (KR); Jeong Hee Kim, Seoul (KR); Kyunghoon Jeong, Gwangju (KR)

(73) Assignee: Ahram Biosystems Inc., Seoul (KR)

( * ) Notice: Subject to any disclaimer, the term of this patent is extended or adjusted under 35 U.S.C. 154(b) by 0 days.

(21) Appl. No.: 10/836,376

(22) Filed: Apr. 29, 2004

(65) Prior Publication Data

US 2004/0191830 A1 Sep. 30, 2004

Related U.S. Application Data

(63) Continuation-in-part of application No. PCT/KR02/01900, filed on Oct. 11, 2002.

(30) Foreign Application Priority Data

Oct. 30, 2001 (KR) ...................... 10-2001-0066943

(51) Int. Cl.
*C12M 1/00* (2006.01)
*C12P 19/34* (2006.01)

(52) U.S. Cl. ................... 435/283.1; 435/91.2; 435/91.1

(58) Field of Classification Search ....................... None
See application file for complete search history.

(56) References Cited

U.S. PATENT DOCUMENTS 5,270,183 A 12/1993 Corbett et al.
5,720,923 A 2/1998 Haff et al.
5,786,182 A 7/1998 Catanzariti et al.
5,919,622 A 7/1999 Macho et al.
6,132,996 A 10/2000 Hunicke-Smith
6,168,948 B1 * 1/2001 Anderson et al. ........ 435/287.2
6,586,233 B2 * 7/2003 Benett et al. ............. 435/286.5
2002/0127152 A1 9/2002 Benett et al.
2004/0152122 A1 8/2004 Hwang et al.

FOREIGN PATENT DOCUMENTS

EP 504435 A1 * 9/1992
WO WO 9748818 A1 * 12/1997

OTHER PUBLICATIONS

Kopp et al. "Chemical Amplification: Continuous-Flow PCR on a Chip" Science. May 15, 1998. vol. 280, pp. 1046-1048.*

* cited by examiner

*Primary Examiner*—Kenneth R. Horlick
*Assistant Examiner*—Christopher M. Babic
(74) *Attorney, Agent, or Firm*—Joseph Hyosuk Kim; JHK Law; Robert L. Buchanan

(57) ABSTRACT

The present invention generally relates to methods and apparatuses for amplifying nucleic acid sequences using immobilized DNA polymerase. More particularly, it relates to methods and apparatuses useful for amplifying target nucleic acid sequences by forming a plurality of reaction regions in which polymerase chain reaction (PCR) can occur, positioning immobilized DNA polymerase in a specific reaction region, and circulating DNA through the reaction regions. The present invention provides those methods and apparatuses that allow simple separation and recovery of the DNA polymerase after the amplification, that can be operated not only with thermostable DNA polymerases but also with non-thermostable DNA polymerases, and that are simpler in their designs and processes so that they can be readily integrated into complex devices such as Lab-on-a-chip.

26 Claims, 6 Drawing Sheets

SEQUENCE LISTING

```
<160> NUMBER OF SEQ ID NOS: 4

<210> SEQ ID NO 1
<211> LENGTH: 17
<212> TYPE: DNA
<213> ORGANISM: Artificial Sequence
<220> FEATURE:
<223> OTHER INFORMATION: Primer

<400> SEQUENCE: 1

cgaggtcgac ggtatcg                                                    17


<210> SEQ ID NO 2
<211> LENGTH: 65
<212> TYPE: DNA
<213> ORGANISM: Artificial Sequence
<220> FEATURE:
<223> OTHER INFORMATION: Primer

<400> SEQUENCE: 2

tctagaacta gtggatcctt ttcttttctt gaattctttc ttttctttta tcgataccgt     60

cgacc                                                                 65


<210> SEQ ID NO 3
<211> LENGTH: 17
<212> TYPE: DNA
```

-continued

```
<213> ORGANISM: Artificial Sequence
<220> FEATURE:
<223> OTHER INFORMATION: Primer

<400> SEQUENCE: 3

attaaccctc actaaag                                                    17


<210> SEQ ID NO 4
<211> LENGTH: 17
<212> TYPE: DNA
<213> ORGANISM: Artificial Sequence
<220> FEATURE:
<223> OTHER INFORMATION: Primer

<400> SEQUENCE: 4

aatacgactc actatag                                                    17
```

METHOD AND APPARATUS FOR AMPLIFICATION OF NUCLEIC ACID SEQUENCES USING IMMOBILIZED DNA POLYMERASE

CROSS REFERENCE TO RELATED APPLICATIONS

The present application is a continuation-in-part application claiming benefit of priority to PCT/KR02/01900, filed on Oct. 11, 2002, the contents of which are incorporated by reference herein in its entirety.

TECHNICAL FIELD

The present invention generally relates to methods and apparatuses for amplifying nucleic acid sequences using immobilized DNA polymerase. More particularly, it relates to methods and apparatuses useful for amplifying target nucleic acid sequences by forming a plurality of reaction regions in which polymerase chain reaction (PCR) can occur, positioning immobilized DNA polymerase in a specific reaction region, and circulating DNA through the reaction regions.

BACKGROUND ART

Nucleic acid sequence amplification technology has a wide application in bioscience, genetic engineering, and medical science for research and development and diagnostic purposes. In particular, the nucleic acid sequence amplification technology using PCR (hereafter referred to as "PCR amplification technology") has been most widely utilized. Details of the PCR amplification technology have been disclosed in U.S. Pat. Nos. 4,683,202; 4,683,195; 4,800,159; and 4,965,188.

Various apparatuses and methods incorporating automated PCR amplification processes have been developed and used for fast and efficient amplification of a variety of genetic samples. The basic working principle of such technology is as follows.

In the commercialized PCR amplification technology, a sample is prepared to contain a template DNA to be amplified, a pair of oligonucleotide primers complementary to a specific sequence of each single strand of the template DNA, a thermostable DNA polymerase, and deoxyribonucleotide triphosphates (dNTP). A specific portion of the nucleic acid sequence of the template DNA is then amplified by repeating a temperature cycle that sequentially changes the temperature of the sample. Typically, the temperature cycle consists of three or two temperature steps, and the amplification processes during the temperature cycle occur in the following manner. The first step is the denaturation step in which the sample is heated to a high temperature and double stranded DNA molecules become separated into single stranded DNA molecules. The second step is the annealing step in which the sample is cooled to a low temperature and the single stranded DNA molecules formed in the first step bind to the primers, forming partially double stranded DNA-primer complexes. The last step is the polymerization step in which the sample is maintained at a suitable temperature and the primers in the DNA-primer complexes are extended by the action of the DNA polymerase, generating new single stranded DNA molecules that are complementary to each of the template DNA strands. The target nucleic acid sequences as selected by the sequences of the two primers are replicated during each cycle consisting of the above three steps. Typically, several millions or higher number of copies of the target nucleic acid sequences can be produced by repeating the temperature cycles for about 20 to 40 times.

The temperature of the denaturation step is typically 90~94° C. The temperature of the annealing step is controlled appropriately according to the melting temperatures ($T_m$) of the primers used, and it typically ranges from 40 to 60° C. It is typical to set the temperature of the polymerization step to 72° C. and use a three-step temperature cycle, since the most frequently used Taq DNA polymerase (a thermostable DNA polymerase extracted from *Thermus aquaticus*) has its optimal activity at that temperature. A two-step temperature cycle in which the polymerization temperature is set to the same as the annealing temperature, can also be used since the Taq DNA polymerase has its polymerase activity in a broad temperature range.

The prior nucleic acid sequence amplification methods have a number of drawbacks as they operate to change the temperature of the whole sample including DNA polymerase according to the three- or two-step temperature cycle.

Firstly, since DNA polymerase is included in the sample in the prior nucleic acid amplification methods, it is not simple to remove the DNA polymerase for purification of the sample after the amplification reaction, and also difficult to reuse the used enzyme.

Secondly, the prior nucleic acid sequence amplification methods can only use thermostable DNA polymerases such as Taq DNA polymerase. This is because the prior apparatuses have the process of heating the whole sample to a high temperature.

Thirdly, it is difficult to incorporate the prior nucleic acid sequence amplification method into a complex device such as Lab-on-a-chip, a miniaturized device that can perform multiple reactions and processes within a chip either simultaneously or sequentially. The prior nucleic acid sequence amplification method is disadvantageous for miniaturization since it requires processes of changing the temperature of the whole sample, thereby having a complex design and processes. Moreover, it is difficult to incorporate the prior method into a complex device in which rapid temperature change is not desirable.

Among various possibilities, a method useful for resolving the problems described above is one using immobilized DNA polymerase. By the term "immobilized enzyme" is meant an enzyme that is physically or chemically bound to a supporting material with its enzyme activity preserved. There are generally a number of advantages of using immobilized enzymes. Firstly, the sample purification process can be simplified since the enzyme can be readily separated and recovered from the reaction solution by removing the supporting material to which the enzyme is immobilized. Secondly, the cost can be reduced since the recovered immobilized enzyme can be reused. Thirdly, the efficiency of the reaction processes can be improved since multiple reaction processes comprising the enzyme reaction(s) can be simplified. In addition, immobilization of the enzyme may result in incidental effects such as improvement of the physical stability of the enzyme or change in the reaction conditions of the enzyme, which in turn may improve the applicability of the enzyme. Therefore, one can expect that the problems associated with the prior nucleic acid amplification methods described above can possibly be resolved by using immobilized DNA polymerase.

However, no method using an immobilized enzyme has been known yet in the prior art to solve the above problems. This is mainly due to two reasons: difficulty in preserving the activity of the immobilized enzyme and development of processes suitable for using the immobilized enzyme. Firstly, various methods has been reported for immobilization of enzymes, but no method has been reported yet for preparation of the immobilized DNA polymerase having high enough activity to produce detectable amount of reaction products in the PCR process. Therefore, in order to realize a nucleic acid amplification method and an apparatus thereof, a method should be developed first to prepare an immobilized DNA polymerase with its activity highly preserved. Secondly, even if an immobilized DNA polymerase preserving a high activity can be used, the prior methods of the temperature cycle type have limitations. For instance, non-thermostable DNA polymerases cannot be used in the prior temperature cycle type methods because the prior methods require a step of heating the whole sample to a high temperature. Moreover, in the prior methods, the polymerization reaction by DNA polymerase can occur only in one temperature step, namely the polymerization step. That is, the polymerization reaction can only occur for a partial period of the total reaction time. The temporal efficiency of the prior methods is thus limited by the speed of changing the temperature during the temperature cycle. Therefore, it is necessary to develop a new nucleic acid sequence amplification method and an apparatus thereof that are not of the prior temperature cycle type in which temperature of the whole sample is changed sequentially, but that are of a different type in which the advantages of using the immobilized DNA polymerase can be incorporated.

DISCLOSURE OF INVENTION

It is an objective of the present invention to provide new methods and apparatuses for amplifying nucleic acid sequences using immobilized DNA polymerase.

More particularly, it is an objective of the present invention to provide nucleic acid sequence amplification methods and apparatuses thereof, wherein immobilized DNA polymerase is used and thus the DNA polymerase can be readily separated and recovered after amplification. The present invention thus provides nucleic acid amplification methods and apparatuses that allow easy purification of the sample and reuse of the DNA polymerase.

It is another objective of the present invention to provide nucleic acid sequence amplification methods and apparatuses using immobilized DNA polymerase, wherein not only thermostable DNA polymerases but also non-thermostable DNA polymerases can be used. As various DNA polymerases can be used, the nucleic acid amplification methods and apparatuses of the present invention can be used for a wider range of applications. In particular, it is an objective of the present invention to provide nucleic acid amplification methods and apparatuses, wherein non-thermostable DNA polymerases can be used so that the accuracy of the nucleic acid replication can be improved.

It is another objective of the present invention to provide nucleic acid sequence amplification methods and apparatuses using immobilized DNA polymerase that are simple in their designs and processes. This can be accomplished by providing methods and apparatuses that do not require the temperature change processes incorporated in the prior nucleic acid sequence amplification methods and apparatuses. The present invention thus provide methods and apparatuses that can be readily miniaturized and also integrated into a complex device such as Lab-on-a-chip as compared to the prior methods and apparatuses.

Others objects and advantages of the invention will become clear to those skilled in the art from the following detailed description, claims, and drawings.

In order to achieve the above objectives, the present invention provides new nucleic acid sequence amplification methods and apparatuses using immobilized DNA polymerase as described below.

More particularly, the present invention provides a method useful for amplifying at least one target DNA sequence using PCR, which method comprises:

a) a step of maintaining a first reaction region at a temperature range suitable for separating double stranded DNA molecules into single stranded DNA molecules,
   a second reaction region at a temperature range suitable for hybridization of the single stranded DNA molecules with primers that are complementary to specific portions of the single stranded DNA molecules so as to form partially double stranded DNA molecules, and
   a third reaction region at a temperature range suitable for DNA polymerization reaction of the primers in the partially double stranded DNA molecules so as to generate primer extension products;

b) a step of positioning an immobilized DNA polymerase in the third reaction region;

and c) a step of circulating the DNA molecules through the first, second, and third reaction regions to make amplification of the target DNA sequences occur, wherein the step of circulating the DNA molecules is repeated at least once.

The present invention also provides an apparatus useful for amplifying at least one target DNA sequence using PCR, which apparatus comprises:

a) a reaction vessel;

b) means for maintaining a first reaction region of the reaction vessel at a temperature range suitable for separating double stranded DNA molecules into single stranded DNA molecules,
   a second reaction region of the reaction vessel at a temperature range suitable for hybridization of the single stranded DNA molecules with primers that are complementary to specific portions of the single stranded DNA molecules so as to form partially double stranded DNA molecules, and
   a third reaction region of the reaction vessel at a temperature range suitable for DNA polymerization reaction of the primers in the partially double stranded DNA molecules so as to generate primer extension products; and c) means for circulating the DNA molecules through the first, second, and third reaction regions to make amplification of the target DNA sequences occur, wherein an immobilized DNA polymerase is positioned in the third reaction region and the circulating means circulates the DNA molecules repeatedly at least once.

The present invention also provides an apparatus useful for amplifying at least one target DNA sequence using PCR, which apparatus comprises:

a) a reaction vessel; and b) means for maintaining a first reaction region of the reaction vessel at a temperature range suitable for separating double stranded DNA molecules into single stranded DNA molecules,
   a second reaction region of the reaction vessel at a temperature range suitable for hybridization of the single stranded DNA molecules with primers that are complementary to specific portions of the single stranded DNA molecules so as to form partially double stranded DNA molecules, and a third reaction region of the reaction vessel at a temperature range suitable for DNA polymerization reaction of the primers in the partially double stranded DNA molecules so as to generate primer extension products; and wherein an immobilized DNA polymerase is positioned in the third reaction region and among the first, second, and third reaction regions, a relatively high temperature region is located lower in height than a relatively low temperature region so that the DNA molecules are circulated repeatedly at least once by thermal convection through the first, second, and third regions to make amplification of the target DNA sequences occur.

EXPLANATION ON THE NUMBERS OF THE IMPORTANT PARTS IN THE DRAWINGS

Figure 1:
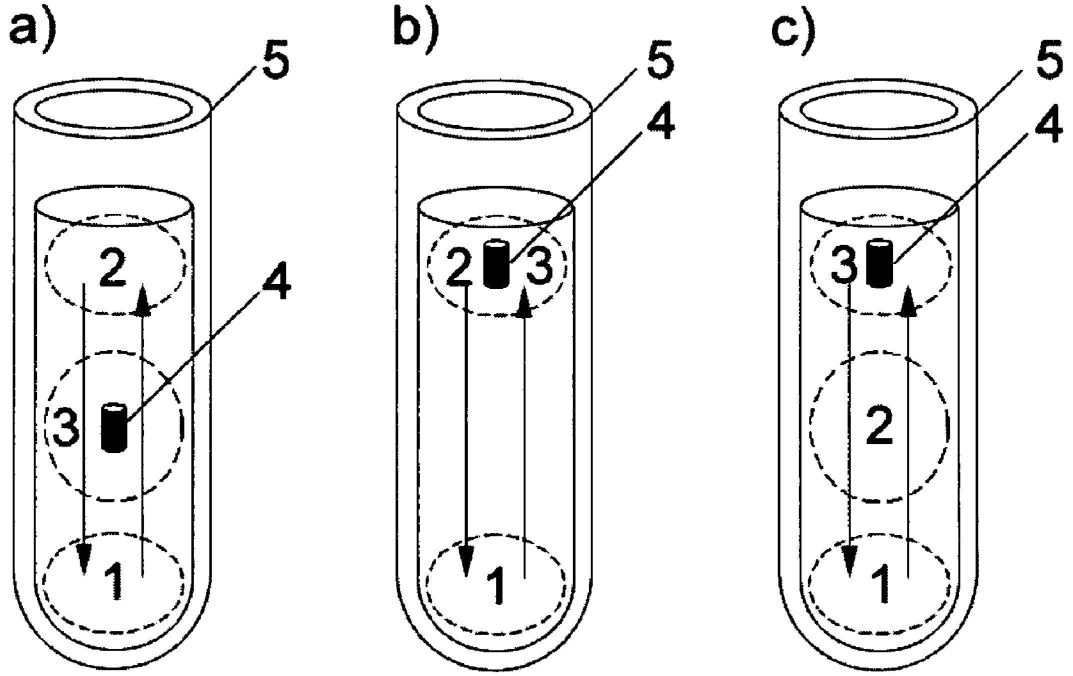
FIG. 1 shows schematic diagrams illustrating the concepts of the nucleic acid amplification methods using immobilized DNA (deoxyribonucleic acid) polymerase according to the present invention.

1: First reaction region
2: Second reaction region
3: Third reaction region
4: Immobilized DNA polymerase
5: Reaction vessel
6: Rectangular wave generator
7, 7': Electrode
8, 8': Piston
9: Magnetic bar
10: Electromagnet-type agitating device
101: First conduction block
102: Second conduction block
103: Reaction vessel
104: Heating device
105: Inlet of temperature control fluid
106: Outlet of temperature control fluid
107: Insulator
112, 117: Through hole
111: Opening

BEST MODE FOR CARRYING OUT THE INVENTION

The term "immobilized DNA polymerase" as used herein is meant a DNA polymerase that is immobilized on a solid support with its polymerase activity preserved. Various methods may be used to prepare the immobilized DNA polymerase, but it should provide an immobilized DNA polymerase that has a high enough polymerase activity so as to enable detection of nucleic acid sequences amplified by PCR of template DNA molecules. The immobilized DNA polymerase used in the example of the present invention was prepared to preserve a high polymerase activity by using a method in which the active site of the DNA polymerase was masked by a DNA substrate and immobilized on a Au surface by covalent bonding. Detailed procedure of the immobilization method is described in the example. The polymerase activity of the immobilized enzyme as prepared by this method was high enough (about 60~80% compared to the solution phase DNA polymerase) to use for PCR. However, immobilized DNA polymerases that can be used with the present invention are not limited to those prepared by the method used in the example of the present invention, but include those prepared by other methods.

In general, the sample used in nucleic acid sequence amplification methods using DNA polymerase comprises a template DNA, four deoxynucleotide triphosphates consisting of dATP, dCTP, dGTP, and dTTP which act as substrates, primers for initiating the polymerization, and a DNA polymerase for catalyzing the polymerization as dissolved in a buffer solution having a suitable salt concentration and pH.

The sample used in the present invention is different in its composition from the sample used in the prior nucleic acid sequence amplification methods. Different from the prior methods where the DNA polymerase is dissolved together in the aqueous sample, the DNA polymerase is not included in the aqueous sample in the present invention since a DNA polymerase that is immobilized on a solid support is used. Therefore, different from the prior methods, it is advantageous that separation of the enzyme and purification of the sample can be easily performed and the enzyme can be reused.

The template DNA used in the present invention may be single stranded, double stranded, or partially double stranded, and it may be a mixture of various DNA molecules having different lengths and shapes. When a nucleic acid sequence of a messenger ribonucleic acid (mRNA) contained in a sample needs to be amplified, a complementary deoxyribonucleic acid (cDNA) typically prepared by converting the RNA to a DNA using a reverse-transcriptase may also be used as a template DNA.

The primers used in the present invention consist of at least one pair of oligonucleotides each containing a portion of the 5' terminus of one of the target nucleic acid sequences in the double stranded DNA to be amplified. Each of the primer pair is designed to hybridize to the 3' terminus of a complementary target nucleic acid sequence in the template DNA and thus to initiate the DNA polymerization. When the polymerization needs to be performed repeatedly, the primers are added in molar excess to the amount of the template DNA. For instance that a target nucleic acid sequence in the template DNA needs to be amplified with a partial modification of the sequence, the primer may be designed to have a nucleic acid sequence having partial substitution, deletion, or addition of the sequence and thus it may not be completely complementary to the template DNA. As far as the modified primer can form a desired hybridized structure with the template DNA, there is no limitation in using such modified primer. This should be apparent to those having ordinary skill in the art to which the present invention pertains.

The main features of the embodiments according to the present invention are: a plurality of reaction regions each maintained at a specific temperature are formed in the sample, and DNA is subject to circulate through the reaction regions.

The DNA polymerization reaction consists of (1) the denaturation step in which double stranded DNA molecules become separated into single stranded DNA molecules; (2) the annealing step in which the primers hybridize with the single stranded DNA molecules each at a specific complementary region to form partially double stranded DNA molecules; and (3) the polymerization step in which the primer extension products are synthesized from the partially double stranded DNA molecules. Amplification of nucleic acid sequences can be achieved by making these three steps occur sequentially and repeatedly. In the prior nucleic acid sequence amplification methods, the above steps are accomplished by changing the temperature of the whole sample sequentially according to the temperature cycle.

In the present invention, however, the above steps are accomplished by forming a plurality of reaction regions each maintained at a specific temperature suitable for each of the above steps and circulating DNA through the reaction regions. The reaction regions consists of 1) a first reaction region maintained at a temperature range suitable for separating double stranded DNA molecules into single stranded DNA molecules, 2) a second reaction region maintained at a temperature range suitable for hybridization of the single stranded DNA molecules with primers that are complementary to specific portions of the single stranded DNA molecules so as to form partially double stranded DNA molecules, and 3) a third reaction region maintained at a temperature range suitable for polymerization of the primers in the partially double stranded DNA molecules so as to generate primer extension products. The three reaction regions and their temperature ranges may overlap each other either partially or completely.

The DNA molecules become denatured into single stranded DNA molecules in the first reaction region and anneal with the primers in the second reaction region. An immobilized DNA polymerase is positioned in the third reaction region to make the polymerization occur, thereby generating the primer extension products. The primer extension products thus generated may have the same nucleic acid sequences, or partially substituted, deleted, or added sequences as compared to the specific portions of the template DNA molecules, depending on the compositions of the primers. Once the PCR process occurs, the primer extension products in addition to the template DNA molecules can also act as templates. Therefore, nucleic acid sequences having the same sequences as the primer extension products are thus amplified afterward.

In the present invention, DNA molecules are circulated through the first, second, and third reaction regions so that amplification of specific nucleic acid sequences can occur. The DNA molecules to be circulated include the primer extension products in addition to the template DNA molecules. These DNA molecules are those that are circulated repeatedly through the reaction regions. Other entities of the sample such as the buffer, deoxyribonucleotide triphosphates, etc. may be located in each of the reaction regions or they may be circulated together with the above DNA molecules. By the clause "the DNA molecules are circulated so that amplification of specific nucleic acid sequences can occur" is meant that the DNA molecules are circulated through the three reaction regions at least once for each of the reaction regions so that the PCR process can occur.

The enzyme that is immobilized in the present invention is an enzyme that has a polymerase activity of replicating a sequence complementary to a template DNA. Such enzyme may be selected from the group consisting of *E. Coli* DNA polymerase I, Klenow fragment of *E. Coli* DNA polymerase I, T4 DNA polymerase, Taq DNA polymerase, and their homologs and derivatives.

Since the prior DNA sequence amplification methods and apparatuses of the temperature cycle type incorporate the step of heating the whole sample to a high temperature, enzymes that are thermostable may only be used practically for the polymerization. If the enzyme used is not thermostable, the enzyme should be added for each temperature cycle due to the heat-induced loss of the enzyme activity. In the present invention, such problem of heat-induced damaging of DNA polymerase is resolved by locating an immobilized DNA polymerase in a region at a specific temperature range (e.g., the third reaction region). More specifically, the enzyme is located in a reaction region maintained at a temperature range suitable for the polymerization, thereby avoiding the undesirable effect due to the denaturation process that requires a high temperature above 90° C. Since the DNA polymerase is not exposed to a high temperature, DNA polymerases that are not thermostable can also be used in the present invention.

The objectives, features and advantages described above will be apparent from the following detailed description provided in connection with the attached drawings. In describing the present invention, detailed explanation on the related prior art will be omitted when it can unnecessarily make the points of the present invention ambiguous. Below, preferred embodiments according to the present invention are explained in detail with reference to the attached drawings.

FIG. 1 shows schematic diagrams illustrating the concepts of the nucleic acid amplification methods using immobilized DNA polymerase according to the present invention. In one embodiment as illustrated in FIG. 1*a*, the first reaction region 1 is maintained at a temperature range suitable for separating double stranded DNA molecules into single stranded DNA molecules, the second reaction region 2 is maintained at a temperature range suitable for hybridization of the single stranded DNA molecules with primers that are complementary to specific portions of the single stranded DNA molecules so as to form partially double stranded DNA molecules, and the third reaction region 3 is maintained at a temperature range suitable for polymerization of the primers in the partially double stranded DNA molecules so as to generate primer extension products. In this embodiment, an immobilized DNA polymerase is positioned in the third reaction region and the DNA molecules are circulated through the first, second, and third reaction regions. In some embodiments of the present invention, some of the reaction regions may overlap each other (FIG. 1*b*), and also positions of the reaction regions may be changed (FIG. 1*c*) to facilitate the circulation of the DNA molecules through the reaction regions.

One embodiment of the present invention is explained more specifically below for the case of using Taq DNA polymerase, with reference to FIG. 1*a*.

The first reaction region maintained at 90~94° C. for denaturation is positioned at the lowest height and the second reaction region maintained at 40~60° C. for annealing of the primers is positioned at the highest height. The third reaction region maintained at the optimum temperature of Taq DNA polymerase, e.g., 72° C., is positioned in the middle in between the first and second reaction regions. When the reaction regions are arranged as described above, circulation of the DNA molecules can be achieved by a thermal convection generated by the temperature gradient, since the relatively high temperature region is positioned lower in height than the relatively low temperature region.

More specifically, the denaturation step occurs first in the first reaction region 1. The denatured DNA molecules then move to the second reaction region 2 via thermal convection in the presence of the primers, causing the annealing step to occur subsequently. The polymerization step finally takes place in the third reaction region 3 by the action of the immobilized DNA polymerase 4, when the DNA-primer complexes move through the third reaction region via thermal convection. Consequently, the three steps of the PCR process, the denaturation, annealing, and polymerization steps, can occur sequentially and repeatedly, thereby achieving an efficient amplification of the target nucleic acid sequences from the sample DNA.

Another embodiment of the present invention is explained below for the case of using Taq DNA polymerase with reference to FIG. 1*b*. Taq DNA polymerase is known to have its optimal activity at 72° C. and its activity remaining in a broad temperature range extending to a low temperature region. Therefore, if Taq DNA polymerase is to be used, the second and third reaction regions may be positioned at the same location by selecting the temperature ranges for the polymerization and the annealing to be the same, as depicted in FIG. 1*b*. Circulation of DNA in this example can also be achieved by thermal convection generated by the temperature gradient.

Another embodiment of the present invention is explained below for the case of using immobilized *E. Coli* DNA polymerase with reference to FIG. 1*c*. *E. Coli* DNA polymerase has its optimal activity at 37° C., which is lower than the annealing temperature of the primer. Therefore, if *E. Coli* DNA polymerase is to be used, it is preferred that the third reaction region where the polymerization occurs be positioned higher in height than the second reaction region where the annealing occurs, as depicted in FIG. 1*c*. Circulation of the DNA molecules in this example can also be achieved by thermal convection generated by the temperature gradient.

In the embodiments depicted in FIGS. 1*a*, 1*b*, and 1*c*, arrangement of the temperatures of the reaction regions 1, 2, and 3 each maintained at a specific temperature range, may not be suitable for generating thermal convection. For such instance, an additional means may be used to circulate the DNA molecules.

Figure 2A:
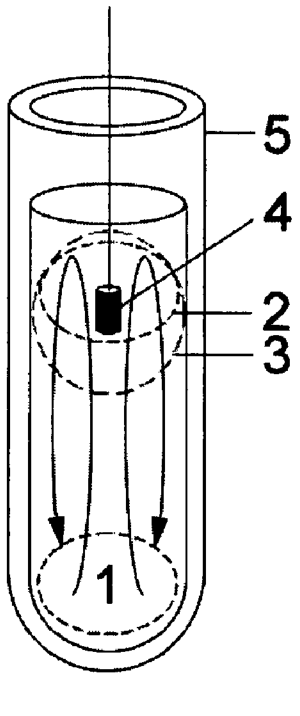
FIG. 2*a* shows a schematic diagram of the nucleic acid amplification method using immobilized DNA polymerase wherein circulation of DNA is induced by thermal convection.

FIG. 2*a* shows one embodiment of the present invention, wherein the DNA molecules are circulated by thermal convection. In this embodiment, the relatively high temperature region is positioned lower in height than the relatively low temperature region and the second and third reaction regions overlap partially each other.

Figure 2B:
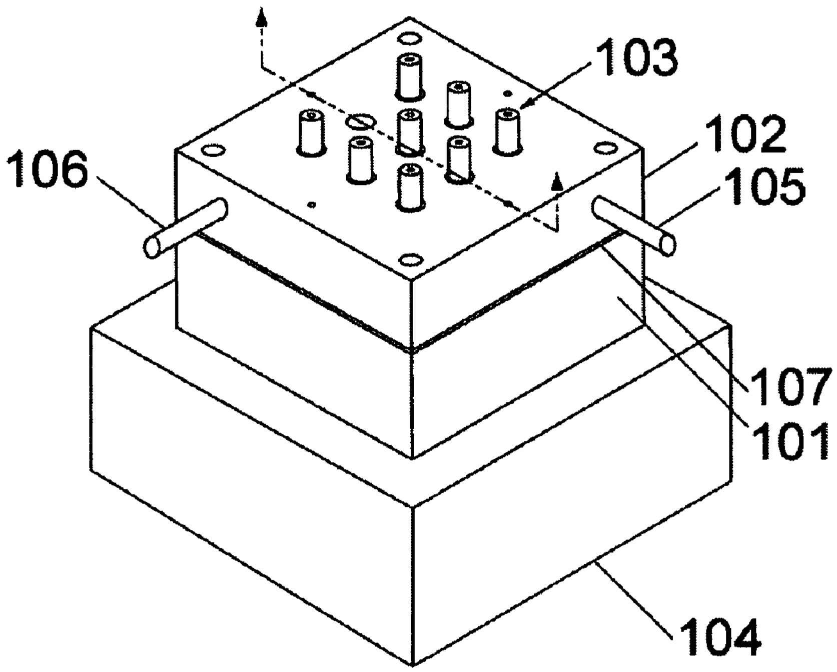
FIGS. 2*b* and 2*c* show a perspective view and a cross sectional view, respectively, of the nucleic acid sequence amplification apparatus using immobilized DNA polymerase wherein circulation of DNA is induced by thermal convection.
Figure 2C:
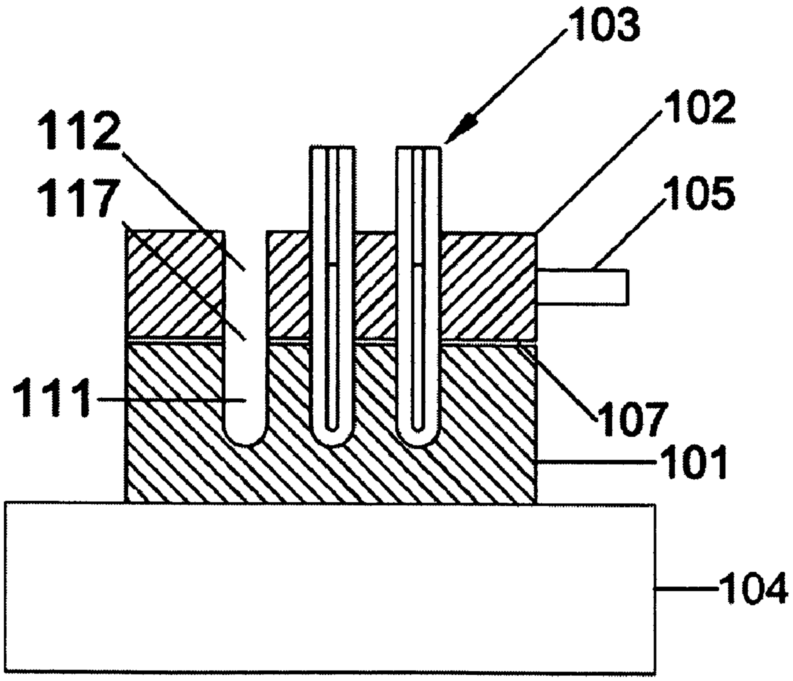

As shown in FIGS. 2*b* and 2*c*, the first conduction block 101 located at the lower position is maintained at a high temperature and the second conduction block 102 located at the higher position is maintained at a low temperature. The two conduction blocks 101 and 102 are thermally insulated each other by using an insulator 107. Under this arrangement, three temperature regions are formed inside the reaction vessel 103 which consist of the first reaction region 1 maintained at a high temperature, the second reaction region 2 maintained at a low temperature, and the third reaction region 3 generated as a result of the temperature gradient between the first and second reaction regions. In this embodiment, the sample in the high temperature region has a lower density than that in the low temperature region. Therefore, a buoyant force is generated and it causes DNA to move from the high temperature region located at the lower position to the low temperature region located at the higher position, while the gravitational force causes DNA to move in the opposite direction. A natural thermal convection is thus generated by the temperature difference, resulting in circulation of DNA through a plurality of the reaction regions 1, 2, and 3. The heating unit 104 used to maintain the first conduction block 101 at the high temperature is depicted only schematically as a block, and a circulating water bath used to maintain the second conduction block 102 at the low temperature is not shown. Details of such embodiment should be apparent to those skilled in the art to which the present invention pertains. In this particular example, two conduction blocks 101 and 102, a heating unit, and a circulating water bath are used as means for maintaining the temperatures of the first, second, and third reaction regions at specific temperature ranges. However, the temperature maintaining means are not limited to the conduction blocks 101 and 102, the heating unit, and the circulating water bath. For instance, instead of the conduction block, a fluid such as liquid or gas at a suitable temperature may be contacted to a specific portion of the reaction vessel or an infrared radiation generating means may be used to directly heat the sample in order to generate a reaction region. Detailed composition of the temperature maintaining means can be modified in various ways depending on the change in the reality of the industrial technology. Any such modifications are obviously included in the scope of the present invention as long as the first, second, third reaction regions can be maintained at the specific temperature ranges.

Figure 3A:
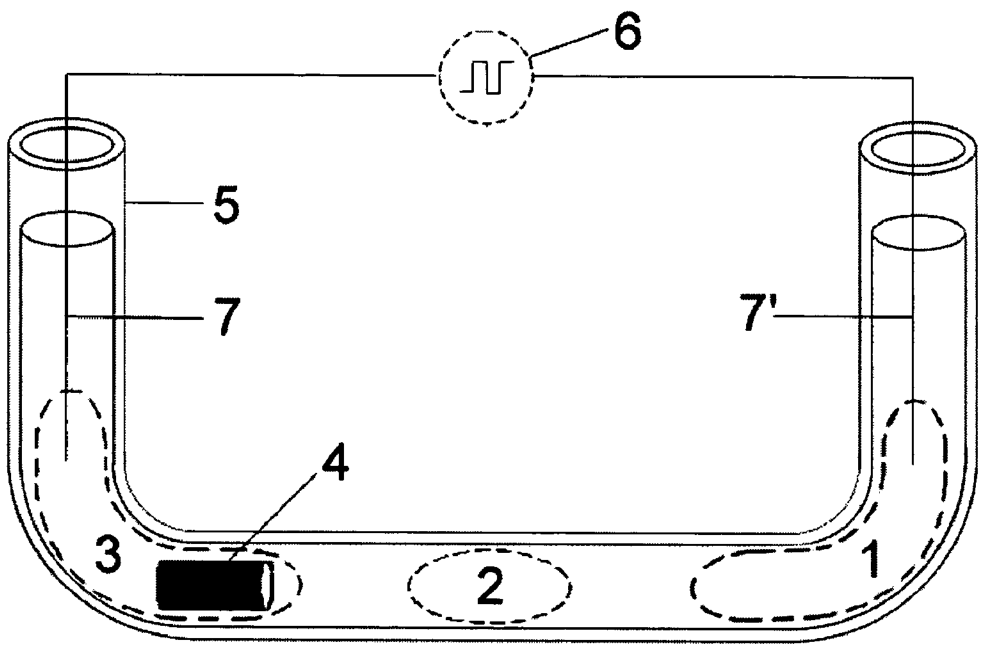
FIGS. 3*a* and 3*b* show schematic diagrams of the nucleic acid sequence amplification methods using immobilized DNA polymerase wherein circulation of DNA is induced by an electric field generating means.
Figure 3B:
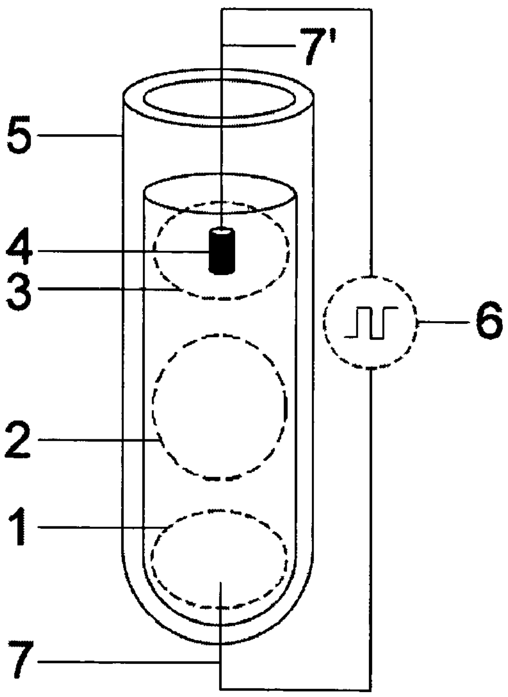

FIGS. 3*a* and 3*b* depict other embodiments of the present invention, wherein an electric field is used to circulate DNA.

DNA has various functional groups having charges in their structures. However, in overall, DNA has a large quantity of negative charges in buffer solution at near neutral pH, because the nucleotides each having one phosphate affect the charge state of DNA most significantly. Therefore, as depicted in FIGS. 3*a* and 3*b*, electrodes 7 and 7' may be introduced to both end regions 1 and 3 of the sample solution and an electric potential difference may be generated and altered periodically inside the sample using a rectangular wave generator 6. By such arrangement, DNA having negative charges can be circulated through each of the reaction regions 1, 2, and 3 sequentially, thereby accomplishing amplification of nucleic acid sequences. Although not shown in FIGS. 3*a* and 3*b*, electrodes may be introduced in each and every one of the reaction regions 1, 2, and 3, or the arrangement of the reaction regions may also be modified.

DNA used as a substrate is the main object of the denaturation, annealing, and polymerization occurring in the DNA polymerization process. Therefore, DNA should be the one that needs to be circulated through the reaction regions. When electric filed is applied to induce movement of DNA, the primers and deoxyribonucleotide triphosphates included in the sample may also move at the same time. However, this also provides conditions preferable for the annealing and polymerization of DNA since these entities also act as substrates and become concentrated in each relevant reaction region. The strength of the electric field and its duration may be selected depending on the size of DNA and the shape of the reaction vessel. If the polymerase is immobilized on a metal surface, the immobilized DNA polymerase itself may be used as an electrode. Detailed embodiments are not limited to those depicted in FIGS. 3*a* and 3*b*, but they can be modified depending on the reaction process, the characteristics of the sample, and the shape of the reaction vessel.

Figure 4:
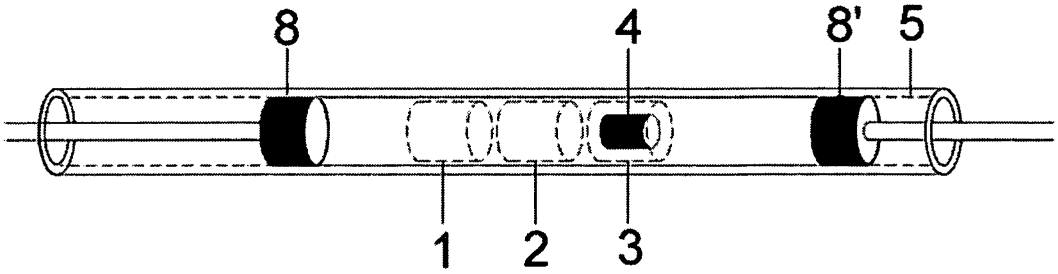
FIG. 4 shows a schematic diagram of the nucleic acid sequence amplification method using immobilized DNA polymerase wherein circulation of DNA is induced by a pressure difference generating means.

FIG. 4 depicts another embodiment of the nucleic acid sequence amplification method according to the present invention, wherein the step of circulating DNA is accomplished by a pressure difference generating means.

As exemplified in FIG. 4, DNA may be circulated through the reaction regions 1, 2, and 3 maintained at specific temperature ranges by generating a pressure difference. The pressure difference may be generated by controlling the pressure applied on one end of the sample inside the reaction vessel 5 higher or lower than that on the other end. FIG. 4 shows a particular example in which pistons 8 and 8' are used to induce a round trip motion. People having ordinary skill in the art to which the present invention pertains can readily recognize that various kinds of liquid or gas pumps may be used in replacement of the pistons 8 and 8' as long as they can generate the desired pressure difference.

Figure 5:
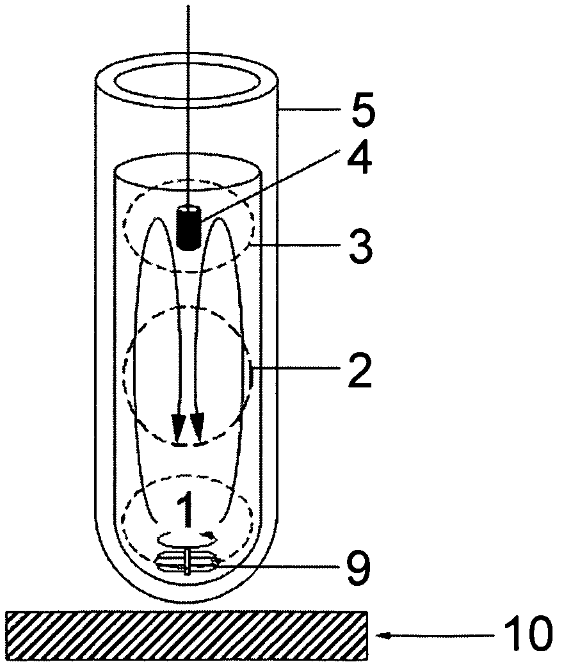
FIG. 5 shows a schematic diagram of the nucleic acid sequence amplification method using immobilized DNA polymerase wherein circulation of DNA is induced by an agitating means.

FIG. 5 depicts another embodiment of the nucleic acid sequence amplification method according to the present invention, wherein the step of circulating DNA is accomplished by an agitating means.

As exemplified in FIG. 5, a magnetic bar 9 may be introduced in the reaction vessel 5 and rotated using an electromagnet-type agitating device 10 to make DNA move. Other agitating device such as a propeller type agitator or a vibrating thin-film agitator that is in contact with the sample solution may also be used to accomplish the purpose of the present invention.

EXAMPLE

A. Preparation of the Immobilized DNA Polymerase

The 65 base single stranded DNA and the KS primer shown below were mixed in a pH 8.3 phosphate buffer at 1:1 molar ratio. The resulting solution was incubated at 94° C. for 10 min and then cooled down slowly below 35° C. During this process, the 65 base single stranded DNA and the KS primer were annealed each other to form a partially double stranded DNA. An appropriate number of moles of Taq DNA polymerase (AmpliTaq Gold) purchased from Perkin Elmer (U.S.A.) was then added to this solution and the resulting mixture was incubated in a dry bath at 72° C. for 10 min. Then, the mixture was moved to a dry bath at 50° C. and incubated for 20 min to finish preparation of a masked DNA polymerase in which the partially double stranded DNA become bound to the active site of the DNA polymerase.

```
KS primer:
5'-CGAGGTCGACGGTATCG-3'            (SEQ ID NO: 1)

65-mer:
3'-CCAGCTGCCATAGCTATTTTCTTTTCTTTCTTA (SEQ ID NO: 2)

AGTTCTTTTCTTTTCCTAGGTGATCAAGATCT-5'
```

In order to have a maximum amount of immobilized DNA polymerase be 0.26 pmol, a Au wire having an outer diameter of 0.1 mm and a length of 4.7 cm was prepared and used after manipulating it to a coil shape having an outer diameter of 1.5 mm and a length of about 4 mm. In order to ensure the cleanness of the surface of the Au wire, it was washed with Piranha solution for 10~15 min at 60~70° C. and was rinsed with deionized water and subsequently with absolute ethanol, right before using.

In order to introduce reaction groups for immobilization onto the Au surface, a monolayer of thiol molecules was formed on the Au surface by using the Au—S bond formation reaction, that is, by using the thiolate formation reaction between a linker molecule having a thiol group and Au, to prepare a supporting material. In this reaction, a mixed solution containing two kinds of thiol molecules having an immobilization reaction group and a non-reactive group, respectively, was used. The mole fraction of the thiol molecule having the immobilization reaction group with respect to the total moles of the two thiol molecules was selected to be 5%. In order to introduce a carboxyl immobilization reaction group, 12-mercaptododecanoic acid having a relatively long alkyl chain was used as a linker molecule. As a thiol molecule having a non-reactive group, 6-mercapto-1-hexanol or 1-heptanethiol was used as a matrix molecule. The carboxyl immobilization reaction group was introduced onto the surface of the Au wire by placing it in 100 μl of a 2 mM mixed thiol solution in ethanol for 2 hours at room temperature and washing it with absolute ethanol.

The Au wire on which the carboxyl immobilization reaction groups were introduced was placed in 120 μl of an ethanol solution containing 10 mM of 1-ethyl-3-(3-dimetylaminopropyl)carbodiimide (EDC) and 5 mM of N-hydroxysuccinimide (NHS) for 2 hours at room temperature. The carboxyl group was activated by reacting with NHS in the presence of EDC and thus forming NHS-ester.

After activating the carboxyl groups of the thiol monolayer, the Au wire was moved to the enzyme solution containing the active-site masked DNA polymerase. In this step, the activated carboxyl (NHS-ester) of the thiol monolayer reacted with the primary amine of the protein, forming an amide bond (—CO—NH—). As a result, the Taq DNA polymerase was immobilized on the supporting material.

The activity of the immobilized DNA polymerase was observed to be 60~80% of that of the solution phase DNA polymerase when examined with the prior PCR method of the temperature cycle type.

B. Preparation of the Reaction Sample

A glass tubing with its one end closed was used as a reaction vessel. The glass tubing had a length of 55~60 mm, an inner diameter of 2 mm, an outer diameter of 8 mm, and a thickness of 3 mm at the bottom-side closed end. The inner wall of the glass tubing was coated with polytetrafluoroethylene using a spray type coating material and thermally hardened.

pBluescript II KS(+) was used as a template DNA to amplify the 164 bp nucleic acid sequence from the nucleotide at the position 627 in the T7 primer region to the nucleotide at the position 790 in the T3 primer region. The sample used in the PCR process contained 40 ng of the template DNA, 40 pmol each of T3 primer (5'-ATTAACCCTCACTAAAG-3') (SEQ ID NO: 3) and T7 primer (5'-AATACGACTCACTATAG-3') (SEQ ID NO: 4), a mixture of 4 nmol of deoxyribonucleotide triphoaphates, 250 nmol of $MgCl_2$, and 50 mM KCl in 10 mM Tris buffer at pH 8.3 with a total volume of 100 μl. The sample was then introduced into the reaction vessel and the Taq DNA polymerase immobilized on the gold wire that was prepared in the step A was positioned in the low temperature region to perform the reaction. As a control for determining the activity of the enzyme after the immobilization, another sample was prepared to have the same composition but with 0.26 pmol of solution phase Taq DNA polymerase added, and the PCR process was performed using the prior temperature cycle method.

C. Example of the DNA Polymerization

Figure 6:
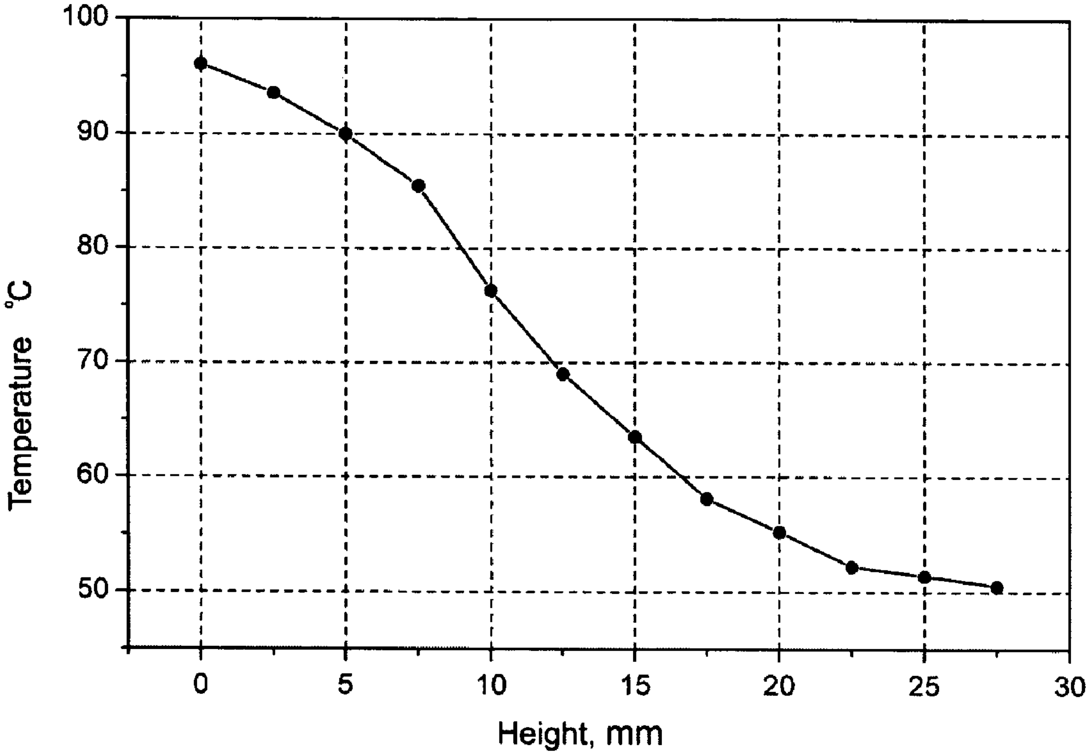
FIG. 6 shows an example of a temperature distribution for the case of forming three reaction regions in the sample according to the present invention.

It is explained with reference to FIGS. 2*b* and 2*c*. The first conduction block 101 located at the lower position was maintained at 96° C. using an electric heater, and the second conduction block 102 located at the upper position was maintained at 45° C. using a circulating water bath. The reaction vessel containing the sample prepared in the step B was inserted into the receptor 111, 117, and 112, and the temperature of each reaction region was measured. From this temperature measurement, it was confirmed (see FIG. 6) that the high temperature region maintained above 90° C. for the denaturation, the low temperature region maintained at about 50° C. for the annealing, and the convection region having a temperature gradient which generate the thermal convention were formed in the sample. Therefore, it is expected that the polymerization will occur in the low temperature region and the upper portion of the convection region.

Figure 7:
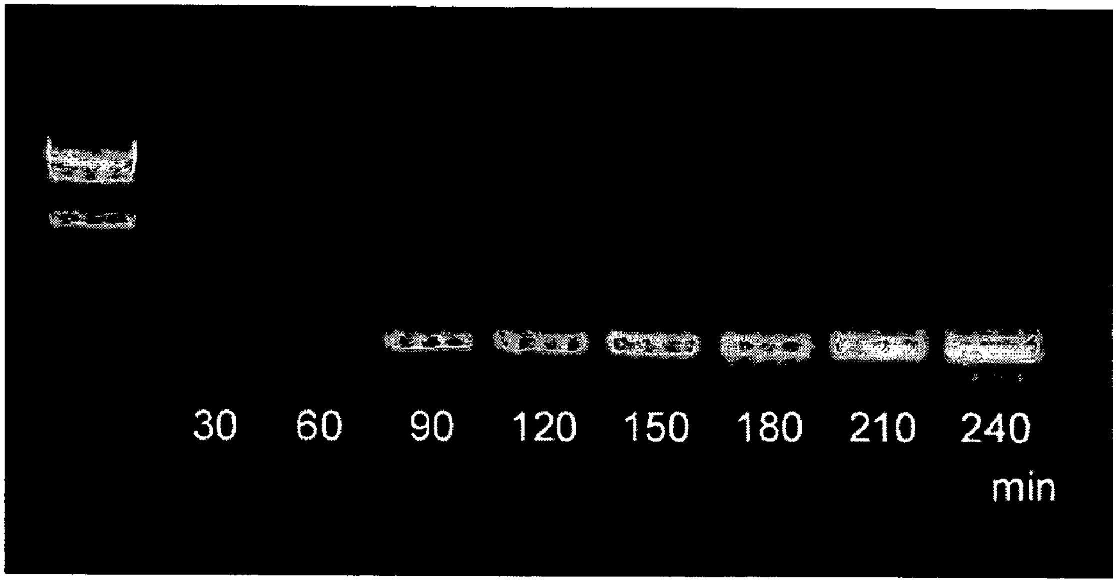
FIG. 7 is a photograph of agarose gel electrophoresis results showing results of the nucleic acid sequence amplification using an immobilized DNA polymerase according to the present invention.

To carry out the polymerization reaction, the coil-shaped gold wire having an outer diameter of 1.5 mm and a length of 4 mm was inserted into the reaction vessel with its center positioned at a location where the temperature was about 55° C., and the sample was incubated under the reaction conditions described above for a selected reaction time. The reaction vessel was then taken out from the apparatus and allowed to cool down. The reaction products were separated by electrophoresis using a 10% agarose gel and stained with ethidium bromide. The DNA products were visualized using fluorescence generated by UV irradiation and quantified with a densitometer. FIG. 7 is a photograph of the electrophoresis results showing the results obtained at every 30 min reaction time up to 4 hr. The reaction product is a 164 bp double stranded DNA. As can be seen in FIG. 7, the PCR process starts to saturate at 120 min.

Those skilled in the art to which the present invention pertains should recognize that the present invention described above is not limited to the foregoing embodiments and the attached drawings and that various substitutions, changes, and modifications are possible without departing from the technical idea of the present invention. Therefore, the foregoing embodiments and the drawings should be taken as examples and should not be interpreted as limitations. The scope of the present invention should be determined by the following claims and is not restricted in any way by the specification.

The present invention has the following advantages.

Firstly, by the use of the immobilized DNA polymerase, the present invention makes it possible to reuse the enzyme repeatedly and also to simplify the process of removing the enzyme in a series of processes. This in turn allows to save the cost and to simplify the related processes.

Secondly, the present invention makes it possible to use DNA polymerases that are not thermostable, such as Klenow fragment and T7 DNA polymerase, thereby extending the application range of the nucleic acid sequence amplification method and apparatus. In particular, the present invention provides a solution to improve the accuracy of the polymerization for replicating nucleic acid sequences by making it possible to use such non-thermostable DNA polymerases.

Lastly, the present invention provides nucleic acid sequence amplification methods and apparatuses thereof that do not require the temperature change processes required in the prior methods and apparatuses. The present invention thus provides the methods and apparatuses that are simpler in their designs and processes and thus that can be readily miniaturized and integrated into complex devices. Moreover, since the present invention makes the polymerization process occur continuously, it provides a means for improving the speed of the nucleic acid sequence amplification.

What is claimed is:

1. An apparatus useful for amplifying at least one target DNA sequence using PCR, which apparatus comprises:

a) a reaction vessel;

b) means for maintaining a first reaction region of the reaction vessel at a temperature range suitable for separating double stranded DNA molecules into single stranded DNA molecules, a second reaction region of the reaction vessel at a temperature range suitable for hybridization of the single stranded DNA molecules with primers that are complementary to specific portions of the single stranded DNA molecules so as to form partially double stranded DNA molecules, and a third reaction region of the reaction vessel at a temperature range suitable for DNA polymerization reaction of the primers in the partially double stranded DNA molecules so as to generate primer extension products; and c) means for circulating the DNA molecules through the first, second, and third reaction regions to make amplification of the target DNA sequences occur, wherein an immobilized DNA polymerase is exclusively positioned in the third reaction region of the reaction vessel and the circulating means circulates the DNA molecules repeatedly at least once; and further wherein the apparatus comprises an opening adapted to receive the reaction vessel and having a closed end defined by the means for maintaining the first reaction region.

2. An apparatus useful for amplifying at least one target DNA sequence using PCR, which apparatus comprises:

a) a reaction vessel; and b) means for maintaining a first reaction region of the reaction vessel at a temperature range suitable for separating double stranded DNA molecules into single stranded DNA molecules, a second reaction region of the reaction vessel at a temperature range suitable for hybridization of the single stranded DNA molecules with primers that are complementary to specific portions of the single stranded DNA molecules so as to form partially double stranded DNA molecules, and a third reaction region of the reaction vessel at a temperature range suitable for DNA polymerization reaction of the primers in the partially double stranded DNA molecules so as to generate primer extension products; and wherein an immobilized DNA polymerase is positioned in the third reaction region of the reaction vessel and among the first, second, and third reaction regions, a relatively high temperature region is located lower in height than a relatively low temperature region so that the DNA molecules are circulated repeatedly at least once by thermal convection through the first, second, and third regions to make amplification of the target DNA sequences occur; and further wherein the apparatus comprises an opening adapted to receive the reaction vessel and having a closed end defined by the means for maintaining the first reaction region.

3. An apparatus according to claim 1 or 2, wherein the immobilized DNA polymerase is an immobilized enzyme having a polymerase activity of replicating a sequence complementary to a template DNA, selected from the group consisting of *E. Coli* DNA polymerase I, Klenow fragment of *E. Coli* DNA polymerase I, T4 DNA polymerase, and their homologs and derivatives.

4. The apparatus according to claim 1, wherein the circulating means consists of an electric field generating means.

5. The apparatus according to claim 1, wherein the circulating means consists of a pressure difference generating means.

6. The apparatus according to claim 1, wherein the circulating means consists of an agitating means.

7. The apparatus of claim 1 or 2, wherein the immobilized DNA polymerase is masked.

8. The apparatus of claim 1 or 2, wherein the opening further comprises a through hole adapted to receive the reaction vessel.

9. The apparatus of claim 8, wherein the opening is in contact with a first conduction block.

10. The apparatus of claim 9, wherein the opening is in further contact with a second conduction block.

11. The apparatus of claim 1 or 2, wherein the third reaction region is positioned between the first and second reaction regions.

12. The apparatus of claim 1 or 2, wherein the second and third reaction regions are positioned above the first reaction region.

13. The apparatus of claim 1 or 2, wherein the second reaction region is positioned between the first and third reaction regions.

14. The apparatus of claim 1 or 2, wherein the second and third reaction regions overlap.

15. The apparatus of claim 1 or 2, wherein the reaction vessel has a closed bottom end.

16. An apparatus according to claim 1 or 2, wherein the immobilized DNA polymerase is an immobilized enzyme having a polymerase activity of replicating a sequence complementary to a template DNA, selected from the group consisting of Taq DNA polymerase, and homologs and derivatives thereof.

17. The apparatus according to claim 1 or 2, wherein the immobilized DNA polymerase is thermostable.

18. The apparatus according to claim 1 or 2, wherein the immobilized DNA polymerase is non-thermostable.

19. The apparatus of claim 1 or 2, wherein the opening adapted to receive the reaction vessel is immobile.

20. The apparatus of claim 1 or 2, wherein the apparatus further comprises an insulator positioned between the means for maintaining the first and second reaction regions.

21. The apparatus of claim 19, wherein the apparatus further comprises an insulator positioned between the means for maintaining the first and second reaction regions.

22. The apparatus of claim 1 or 2, wherein the apparatus further comprises a gap between a sample and the means for maintaining the third reaction region of the reaction vessel at the temperature range suitable for DNA polymerization reaction.

23. The apparatus of claim 19, wherein the apparatus further comprises a gap between a sample and the means for maintaining the third reaction region of the reaction vessel at the temperature range suitable for DNA polymerization reaction.

24. The apparatus of claim 20, wherein the apparatus further comprises a gap between a sample and the means for maintaining the third reaction region of the reaction vessel at the temperature range suitable for DNA polymerization reaction.

25. The apparatus of claim 20, wherein the reaction vessel has a closed bottom end.

26. The apparatus of claim 22, wherein the reaction vessel has a closed bottom end.

* * * * *